US008163803B2

(12) United States Patent
Martins et al.

(10) Patent No.: US 8,163,803 B2
(45) Date of Patent: Apr. 24, 2012

(54) COMPOUNDS DERIVED FROM LIDOCAINE, PHARMACEUTICAL COMPOSITIONS, USE AND METHOD OF TREATMENT, PREVENTION OR INHIBITION OF DISEASE

(75) Inventors: Marco Aurélio Martins, Rio de Janeiro (BR); Jorge Carlos Santos Da Costa, Rio de Janeiro (BR); Núbia Boechat, Rio de Janeiro (BR); Rodrigo de Azeredo Siqueira, Rio de Janeiro (BR)

(73) Assignee: Fundação Oswaldo Cruz—FIOCRUZ, Rio de Janeiro (BR)

( * ) Notice: Subject to any disclaimer, the term of this patent is extended or adjusted under 35 U.S.C. 154(b) by 1002 days.

(21) Appl. No.: 11/570,234

(22) PCT Filed: Jun. 7, 2005

(86) PCT No.: PCT/BR2005/000101
§ 371 (c)(1),
(2), (4) Date: Nov. 26, 2007

(87) PCT Pub. No.: WO2005/120148
PCT Pub. Date: Dec. 22, 2005

(65) Prior Publication Data
US 2008/0221206 A1 Sep. 11, 2008

(30) Foreign Application Priority Data
Jun. 7, 2004 (BR) .................................. 0404222

(51) Int. Cl.
*A61K 31/167* (2006.01)
(52) U.S. Cl. ....................................................... 514/613
(58) Field of Classification Search ............... 514/237.8, 514/613
See application file for complete search history.

(56) References Cited

U.S. PATENT DOCUMENTS

| | | | |
|---|---|---|---|
| 3,729,470 A | 4/1973 | Vaille | |
| 4,252,804 A | 2/1981 | Joullie et al. | |
| 4,353,914 A | 10/1982 | Kaila et al. | |
| 4,532,249 A | 7/1985 | Molnar et al. | |

FOREIGN PATENT DOCUMENTS

| | | |
|---|---|---|
| CS | 126539 | 3/1968 |
| EP | 0133259 | 2/1985 |
| GB | 2129424 | 5/1984 |

OTHER PUBLICATIONS

Costa et al., "Synthesis and antispasmodic activity of lidocaine derivatives endowed with reduced local anesthetic action," *Bioorganic & Medicinal Chemistry Letters*, 18: 1162-1166, 2008.
Costa et al., "JMF2-1, a lidocaine derivative acting on airways spasm and lung allergic inflammation in rats," *J Allergy Clin Immunol*, 119(1): 219-225, 2007.
Interchim Intermediates (Catalog Name), Publication Date: Jan. 18, 2005, Order No. BAS 00669492; CHEMCATS [online]. Copyright 2005 ACS on STN [retrieved on Dec. 5, 2005]. Retrieved from: STN International, Karlsruhe. Accession No. 2005: 1120634 CHEMCATS. abstract.
International Search Report, PCT Application No. PCT/BR2005/000101, 4 pages.
Lofgren, N. "Local anesthetics. I", Arkiv Kemi, Mineral. Geol. (1946), A22(No. 18), 30 pp. (abstract) CAPLUS [online]. Copyright 2005 ACS on STN [retrieved on Dec. 5, 2005]. Retrieved from: STN International, Karlsruhe. Accession No. 1949:4503. abstract.
Olsen et al., "Lidocaine-derivative JMF2-1 prevents ovalbumin-induced airway inflammation by regulating the function and survival of T cells," *Clinical & Experimental Allergy*, 41: 250-259, 2011.
Udrenaite, E. et al. "Electrophilic substitution of 4-(chloroacetylamino)-1, 3-benzodioxolane,and synthesis of 4-(diethylaminoacetylamino )-1,3-benzodioxolanes substituted in the aromatic ring". Sb. Nauch. Tr. Vuzov Lit SSR. Khimiya i Khim. Tekhnol. (1989), (31), 38-43 From: Reference Zh., Khim. 1990, Abstract No. 10Zh222. (abstract) CAPLUS [online]. Copyright 2005 ACS on STN [retrieved on Dec. 5, 2005]. Retrieved from: STN International, Karlsruhe. Accession No. 1991:6343. abstract.

*Primary Examiner* — Taofiq A Solola
(74) *Attorney, Agent, or Firm* — Klarquist Sparkman, LLP.

(57) ABSTRACT

The present invention relates to lidocaine derived compounds, which present less anesthetic activity than lidocaine itself, but with more anti-inflammatory and spasmolytic activity than said lidocaine as well as pharmaceutical compositions with at least one of these compounds or a salt of those as active principle and to the use of such compositions to treat, prevent or inhibit atopic diseases including asthma, rhinitis, allergic urticaria, chronic lung inflammation associated with eosinophilia, following the example of atopic asthma and chronic intestinal inflammation, as colitis for instance. The pharmaceutical composition may be available in spray form, solution, suspension, emulsion destinated to be applied by nebulization, or in any of the pharmaceutical available forms for oral or injectable use.

10 Claims, 7 Drawing Sheets

COMPOUNDS DERIVED FROM LIDOCAINE, PHARMACEUTICAL COMPOSITIONS, USE AND METHOD OF TREATMENT, PREVENTION OR INHIBITION OF DISEASE

CROSS REFERENCE TO RELATED APPLICATIONS

This is the U.S. National Stage of International Application No. PCT/BR2005/000101, filed Jun. 7, 2005, which was published in English under PCT Article 21(2), and claims benefit of priority of Brazilian Patent Application No. 0404222-0, filed Jun. 7, 2004, both of which are incorporated herein in their entirety.

The present invention relates to lidocaine derived compounds, which present less anesthetic activity than lidocaine itself, but with more anti-inflammatory and spasmolytic activity than said lidocaine as well as pharmaceutical compositions with at least one of these compounds or a salt of those as active principle and to the use of such compositions to treat, prevent or inhibit atopic diseases including asthma, rhinitis, allergic urticaria, chronic lung inflammation associated with eosinophilia, following the example of atopic asthma and chronic intestinal inflammation, as colitis for instance.

Further, the present invention provides with a method of treatment, prevention or inhibition of atopic diseases including asthma, rinithis, allergic urticaria, chronic lung inflammation associated with eosinophilia, following the example of atopic asthma and chronic intestinal inflammation, as colitis for instance, comprehending the administration of a pharmaceutically effective amount, at least one of these compounds, or a salt of those, to the human-being that will need said treatment, prevention or inhibition.

BACKGROUND OF THE INVENTION

In 1884, Karl Koller, Australian ophthalmologist, introduced the use of substances with anesthetic activity in medicine field. From that initial study, the search for natural or synthetic compounds with the property to promote the blocking of neural stimulus transmission has been investigated by a plurality of research groups. In 1935, Southworth and Dabbs, in *Xylocaine: a superior agent for conduction anesthesia*. Curr Res Anesth Analg, 32, 159-170, synthesized alkaloid isomers with anesthetic properties. Subsequently, Löfgren and Takman, in 1952, in the article *Studies on Local Anaesthetics VII*. Acta Chemica Scadinavica, 6, 1010-1015, synthesized a compound that was named lidocaine from that on, such compound has a remarkable local anesthetic activity, whose formula is represented by the formula I:

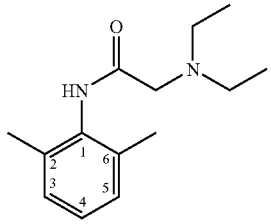

(I)

Lidocaine, 1-(2-(dyethylamine)N-dymethylfenyl)-acetamide, commercially registered under the name Xylocaine®, besides its well-known local anesthetic activity, applied on blocking the process of depolarization of the excitatory membranes, in a mechanism associated with the inhibition of the sodium channels, has useful clinical properties to the control of cardiac arrhytmia, promoting a reduction in the cardiac contractibility and hypotension, reduction and/or inhibition of tumour growth, bactericidal ability and modification of plasma cells, making interferece in virus absorption possible and, thus, providing antiviral effect, according to as described in EP 0643964.

Recent studies, carried out by Hollmann and Durieux, in *Local anesthetics and the inflammatory response: a new therapeutic indication?* Anesthesiology. 2000, 93, 858-875, point out to evidences that local anesthetic agents, including lidocaine, also hold the property of preventing from inflammatory processes. In these cases, however, the modus operandi and, most of all, the potential clinical applicability of these properties remain little explored.

It was verified that bronchoalveolar lavage of patients suffering from asthma often inhibited eosinophils survival stimulated by different cytosines, including the IL-5, as taught by Hunt et al., in *Effect of Nebulized Lidocaine on Severe Glucocorticoid-Dependent Asthma*. Mayo Clin. Proc., 1996, 71, 361-368. Thus, it was confirmed that, in fact; when lidocaine was used in a procedure to collect the bronchoalveolar effluent it was itself responsible for the significant survival block of eosinophils observed in vitro.

Asthma is a complex and heterogeneous inflammatory lung disease that appears strongly associated with a hyperresponsivity to bronchitis, eosinophil infiltrate and recurring episodes of getting short of air, whistling noise in the chest and coughing. Such signs and symptoms are related to the obstruction of the airways that may be spontaneously reversible or after treatment. It is known that a inflammation of the respiratory passages plays an important role in the pathogenesis of the disease. The process is remarkable by the increase in the production of IgE and a polarization of the response Th2 with increasing levels of cytocines type 2, including IL-4, IL-5 and IL-13, besides beta chemokines. An important aspect of asthma pathogenesis is the accumulation of a plurality of eosinophils in the respiratory passages, a phenomenon that occurs in strict correlation with the seriousness of the disease. Since long ago eosinophils have been associated to allergic diseases and there are increasing evidences that they play a pro-inflammatory role.

There are substantial evidences in literature that mediators derived from eosinophils, including basic cationic proteins, cytocines and inflammatory lipidic mediators, would be associated with one another in a direct and causal relation to the symptoms and pathological signs observed in the asthmatic set.

The therapeutical arsenal therapeutic available for the treatment of asthma is relatively ample, but, in general, the medical practice is restricted basically to the use of two classes of medicines; the steroidal anti-inflammatory agents and the bronchodilators type beta 2 adrenergic, both of them are recognized bring benefits, which are limited by a plurality of side effects.

The bronchodilator agents link to the receptors type beta 2 adrenergic located on the surface of the non-striated muscle cells that line the bronchial tubes. This connection activates a complex signaling cascade that results in the reduction of the intracellular levels of calcium and subsequent relaxation of the non-striated muscle, clearing upper respiratory passages and protecting against muscle spasm. However, recent studies point out to a life risk increase in patients that make chronical use of bronchodilators unaccompanied by glucocorticoids. The isolated use of the bronchodilator is of elevated risk, because while it transmits to the patient a relieving sensation of symptoms, it masks the progressive inflammatory picture deterioration.

Epidemiological studies have shown that treatment of asthma with bronchodilators do not prevent the increasing morbidity and mortality. Children with persistent asthma symptoms until adulthood show reduced lung function. Adult patients that suffer from asthmatic bronchitis present na accelerated decline in lung volume. Therefore, there is a tendency to focus the asthma therapy on the inflammatory processes.

In this sense, therapy with glucocorticoids agents is the most effective nowadays in order to control serious asthma because it reduces the allergic response started off by eosinophils and by its anti-inflammatory effects as a result of the modulation of the genic transcription. The connection of these agents to specific receptors present in the cytoplasm of target cells is followed by the translocation of steroidal-receptor complex to the nucleus, dimerization and coupling of the dimer to the so-called "responsive elements of glucocorticoids" in the nuclear DNA, this way activating or restraining the transcription mechanisms. The suppressive effect of the glucocorticoids agents on the transcription of an expressive number of genes of inflammatory mediators, including cytocines (IL-4, IL-5, IL-13, GM-CSF, etc) e chemokines (eotaxin, MCP-1, etc), is well established. Although glucocorticoid agents therapy, in general, is successful to control the symptoms of asthma, the severe systemic effects of these medicaments and the refractory to the treatment presented by a subgroup of asthmatic individuals, point out to a unequivocal necessity of new alternative therapies.

In the literature, there are clear indications that long-term treatment with nebulized lidocaine resulted in relief of asthma symptoms, diminishing the dependency to the treatment with steroidal anti-inflammatory in 20 out of 24 patients investigated (Hunt, L. W., Swedlund, H. A., Gleich, G. J. *Effect of Nebulized Lidocaine on Severe Glucocorticoid-dependent Asthma*. Mayo Clin. Proc., 1996, 71, 361-368).

According to literature, the anti-asthma effect of lidocaine would be associated with its capacity to bring eosinophils to death by apoptosis, eliminating, this way, crucial effector cells for the pathogenesis of asthma.

Besides the acknowledged anti-inflammatory activity, lidocaine presents other actions that, at least in thesis, could contribute to an anti-asthma action. As for example, it affects the respiratory function acting directly on the respiratory passages muscles, modulating intracellular levels of calcium in non-striated muscle fibers. It is well-know that the anti-inflammatory activity of lidocaine is not restricted to the action on the eosinophils. Some studies report its inhibitory action over neutrophyl and monocytes actions, including the synthesis of phosphatidylcholine, tirosine phosphorylation, releasing of superoxide, releasing of lysosome enzymes, phagocytosis, aggregation, adherence to the membrane of endothelial cells and expression/releasing of molecules of cellular adhesion. However, the actions of lidocaine and other local anesthetics on the respiratory passages are heterogeneous and complex. There are strong evidences that lidocaine prevents risky bronchospasm in response to different stimuli induce bronchoconstriction, including instrumentation of respiratory passages, hyperosmolar saline solution, asthma induced by exercise and histamine. It is important to notice that the attenuation of bronchospasm by histamine, observed in patients treated with lidocaine, occurs independently of the anesthetic action, since the local anesthetic dyclonine was ineffective.

In healthy individuals, lidocaine aerosol produces few effects in the pulmonary mechanics. However, individuals with elevated reactivity in the respiratory passages, including asthmatic ones, lidocaine administered through aerosol may induce a remarkable initial bronchoconstrictor effect. At least two hypotheses have been raised to explain this effect apparently paradoxical. First of all, local anesthesia of the respiratory passages could prevent from an appropriate sensorial perception of inspiration and expiration function regulatory mechanisms. Actually, a state of inspiratory incoordination has been reported after anesthesia by lidocaine during the procedures of laryngoscopy with subsequent obstruction of the upper respiratory passages. Secondly, lidocaine could favor the bronchoconstrictive response inhibiting bronchodilators neurogenic reflexes, mediated by sympathetic innervation and others.

On the other hand, the use of lidocaine in the treatments of asthma presents the disadvantage of the anesthetic activity characteristic of this molecule.

It is therefore evident that there are inconvenient effects when using lidocaine in the treatment of asthma, since it causes discomfort to the patients.

As a consequence, there is the necessity to provide alternatives in order to overcome the inconvenients previously pointed out.

In this way, it constitutes one of the main characteristics of the present invention: the development of compounds with anti-inflammatory and spasmodic effectiveness similar or superior to the one made evident by lidocaine, but with local anesthesia minimized.

SUMMARY OF THE INVENTION

Considering the blocking of nervous conveyance in the lung it has been associated with side effects of medicaments according to the previous description, it is an objective of the present invention to provide lidocaine derived compounds similar in structure, or salts from said structures, with anti-inflammatory and spasmodic effectiveness and power superior or comparable to the ones observed as to lidocaine, but with local anesthetic action and minimized side effects. A plurality of derivatives was synthetized and had their pharmacological activity evaluated in comparisons with lidocaine.

These compounds present local anesthetic activity ranging from 19% to 60% out of the one evidenced by lidocaine. However, they present spasmodic capacity as well as potency to stabilize mast cells from 7 to 100 times higher than those presented by lidocaine, further comparable actions in terms of blocking the increase of vascular permeability and eosinophils infiltrate, caused by antigenic challenge. In addition, all the compounds evaluated in the present invention presented a convulsivant activity remarkably inferior to the one observed as to lidocaine. In a whole, such pharmacological properties support lidocaine derivatives hereby presented in order to constitute a new alternative in the anti-asthma and anti-allergy therapy with distinct advantages over local anesthetics.

An objective of the present invention relates to lidocaine derived compounds or their pharmaceutically acceptable salts, the same, represented by one of the formulas (II), (III) e (IV):

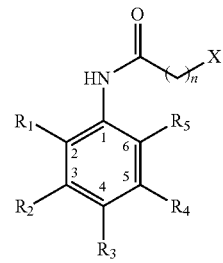

DESCRIPTION OF THE INVENTION

The present invention relates to lidocaine derived compounds, that are hereby represented by one of the following formulas (II), (III) e (IV):

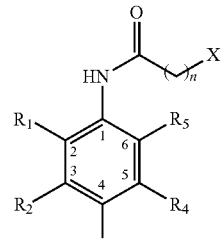
(II)

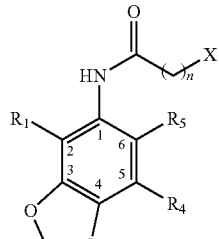
(III)

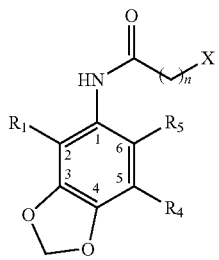
(III)

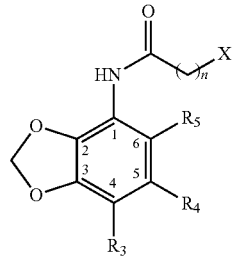
(IV)

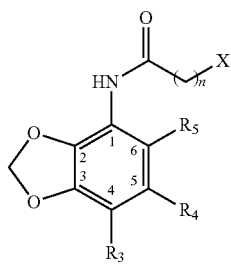
(IV)

where the radicals $R_1$, $R_2$, $R_3$, $R_4$, and $R_5$ are represented by H, $CH_3$, $CF_3$ or OR;

where the radical R, in any position of the aromatic ring or the side chain, may be represented by hydrogen, alkylic groups with 1 or more atoms of carbon in straight or branched chain, alkenes or alkynes, hydroxyl, hydroxyalkyl or oxygen functions in cyclic or acyclic systems forming a heterocyclic ring, free or substitued amines, tioalkyl, donor groups and electron attractor, halogens or N donor groups;

"n" may be constituted by 1 or up to 4 atoms of carbon to separate; and, the radical X may be represented by:

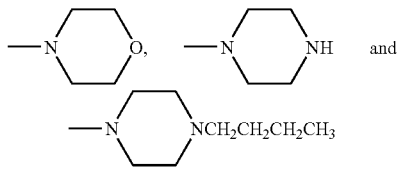

Another objective of the present invention relates to a pharmaceutical composition including, as active principle, at least one of the lidocaine derived compounds represented by the formulas (II), (III) and (IV).

A further objective of the present invention relates to the use of such compositions in the treatment, prevention of inhibition of atopic diseases, which includes asthma, rhinitis, allergic urticaria, chronic lung inflammation associated with eosinophilia, following the example of non-atopic asthma and chronic intestinal inflammation, as colitis for instance.

Another objective of the present invention relates to a method of treatment, prevention of inhibition of atopic diseases, which includes asthma, rhinitis, allergic urticaria, chronic lung inflammation associated with eosinophilia, following the example of non-atopic asthma and chronic intestinal inflammation, as colitis for instance, comprising the use of a therapeutical effective amount of a pharmaceutical composition for the human being who needs the referred treatment, prevention or inhibition, according to the description in the present invention.

where the radicals $R_1$, $R_2$, $R_3$, $R_4$, and $R_5$ are represented by H, $CH_3$, $CF_3$ or OR;

where the radical R, in any position of the aromatic ring or the side chain, may be represented by hydrogen, alkylic groups with 1 or more in straight or branched chain atoms of carbon, alkenes or alkynes, hydroxyl, hydroxyalkyl or oxygen functions in cyclic or acyclic systems forming a heterocyclic ring, free or substituted amines, tioalkyl, donor groups and electron attractors, halogens or N donor groups;

"n" may be constituted by 1 or up to 4 atoms of carbon to separate; and, the radical X may be represented by:

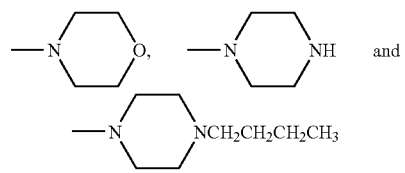

In the present invention all the compounds are presented in either their free base form or pharmaceutically acceptable salts, preferably chloridates.

More especifically, lidocaine derived compounds may be selected among:
2-dyethylamine-2',3'-acetoxylidide;
2-dyethylamine-2',4'-acetoxylidide;
2-dyethylamine-2',5'-acetoxylidide;
2-dyethylamine-2-trifluormethylacetoanilide;
2-dyethylamine-3',5'-acetoxylidide;
2-dyethylamine-3',4'-acetoxylidide;
2-morpholin-2',6'-acetoxylidide;
2-piperidine-2',6'-acetoxylidide;
2-N-butyl-piperidine-2',6'-acetoxylidide;
2-dyethylamine-2',3'-methylenodioxy-acetoanilide;
2-dyethylamine-3',4'-methylenodioxy-acetoanilide;
2-dyethylamine-2',6'-dimetoxy-acetoanilide;
2-dyethylamine-2',3'-dimetoxy-acetoanilide;
2-dyethylamine-2',4'-dimetoxy-acetoanilide;
2-dyethylamine-2',5'-dimetoxy-acetoanilide;
2-dyethylamine-3',4'-dimetoxy-acetoanilide; and,
2-dyethylamine-3',5'-dimetoxy-acetoanilide;
which are lidocaine derivatives or a pharmaceutically acceptable salt of the same, preferably chloridate, in combination with a pharmaceutically acceptable vehicle.

The compounds above present biological activity, as for example the pharmacological activity, which includes, but it is not limited to a local anesthetic activity minimized when compared to lidocaine. Other examples of pharmacological activities of said compounds are the anti-inflammatory and the spasmodic activities.

The compounds presented in this invention may be synthetized accordingly to well-known processes by an expert in the field, as described in the patents U.S. Pat. No. 2,441,498, GB706.409 and GB758.224, but always observing the balance between the intrinsec lipophilic and hydrophilic characteristics of themselves, considering the same, influence the anesthetic activity.

Pharmaceutical compositions with at least one of the compounds in the present invention, or a salt of these compounds, may be administered through pharmaceutical forms as spray, solution, suspension, emulsion destinated to be applied by nebulization or pharmaceutical form of oral administration or through injections prepared with a solution or suspension of at least one of the compounds in the present invention in a concentration between 0.5 and 40% p/v, and a pharmaceutically acceptable vehicle, in order to produce an appropriated dose. These compositions to treat, prevent or inhibit atopic diseases including asthma, rhinitis, allergic urticaria, chronic lung inflammation associated with eosinophilia, following the example of non-atopic asthma and chronic intestinal inflammation, as colitis for instance.

BRIEF DESCRIPTION OF THE FIGURES

In order to better understand the invention, it is listed as follows the Figures and a brief description of said Figures.

In order to help understand the examples and Figures, the following compounds are named according to reference codes:

| Compounds | Code |
| --- | --- |
| 2-dyethylamine-2',3'-acetoxylidide | JM23-1 |
| 2-dyethylamine-2',4'-acetoxylidide | JM24-1 |
| 2-dyethylamine-2',5'-acetoxylidide | JM25-1 |
| 2-dyethylamine-2-trifluormetilacetotoluidide | JMF2-1 |

Figure 1:
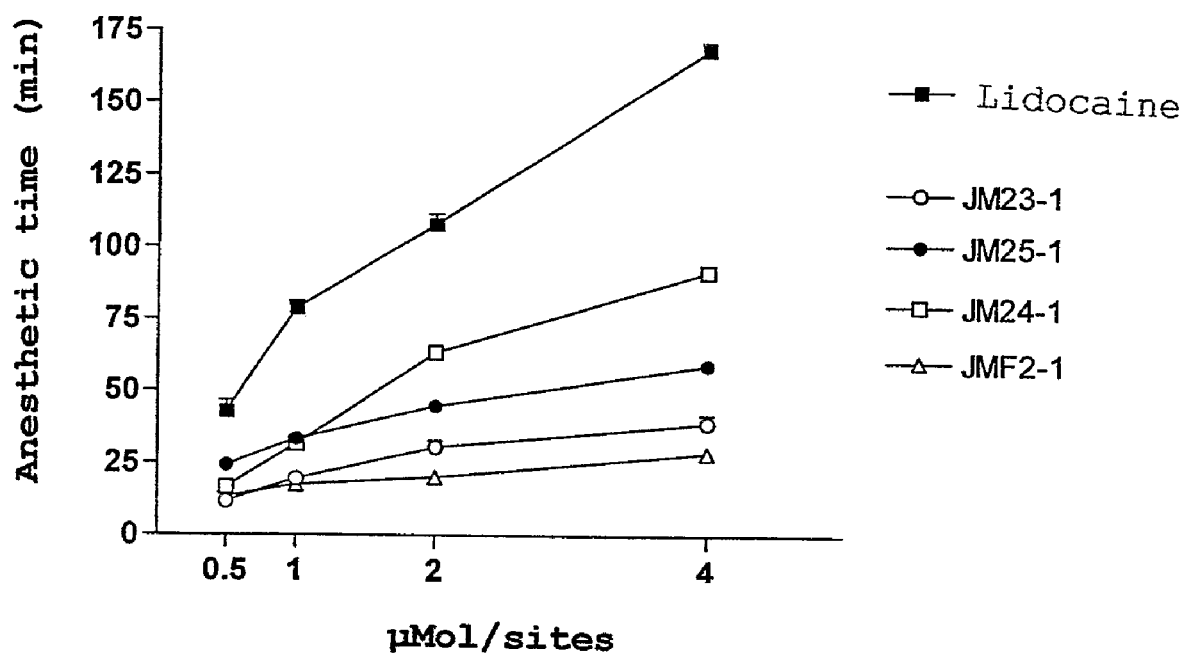

FIG. 1—local anesthetic effect of lidocaine and its derivatives evaluated in cutaneous sites of the dorsal region of adult Wistar rats, according to previously established experiment.

Figure 2:
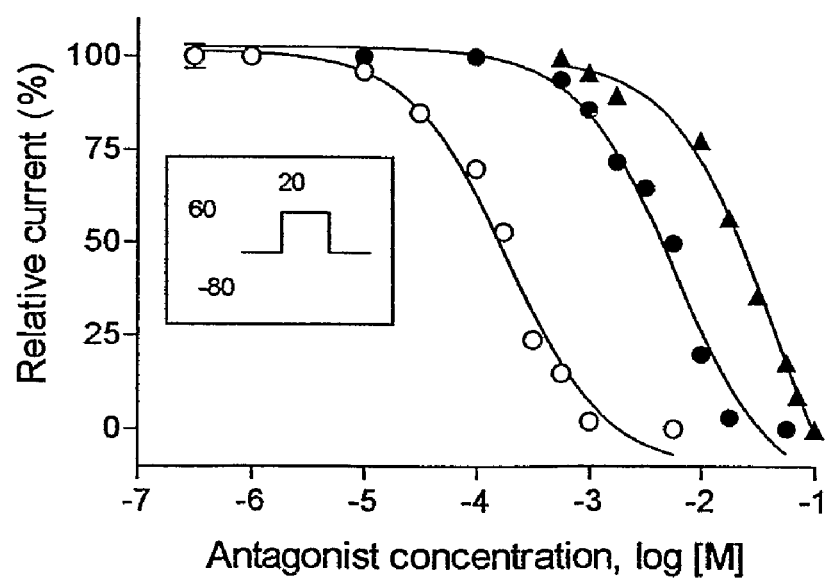

FIG. 2—Tonic block of $Na^+$ currents in $GH_3$ cells by external perfusion of lidocaine (○), JM24-1 (●) and JMF2-1 (▲).

Figure 3:
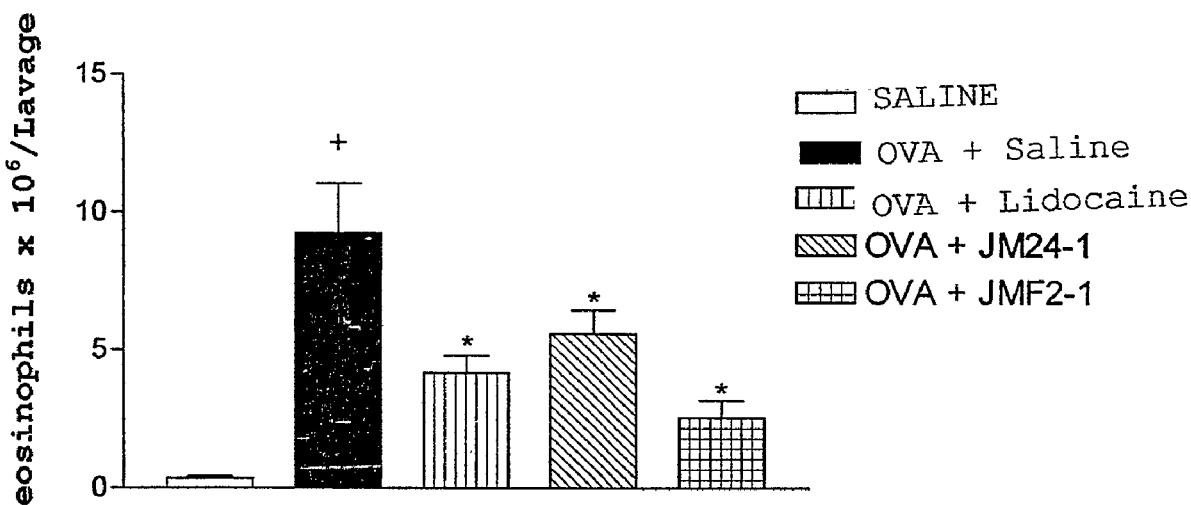

FIG. 3—Inhibitory effect of lidocaine and its derivatives on pulmonary eosinophilia caused by stimulation allergenic em experimental animals.

Figure 4:
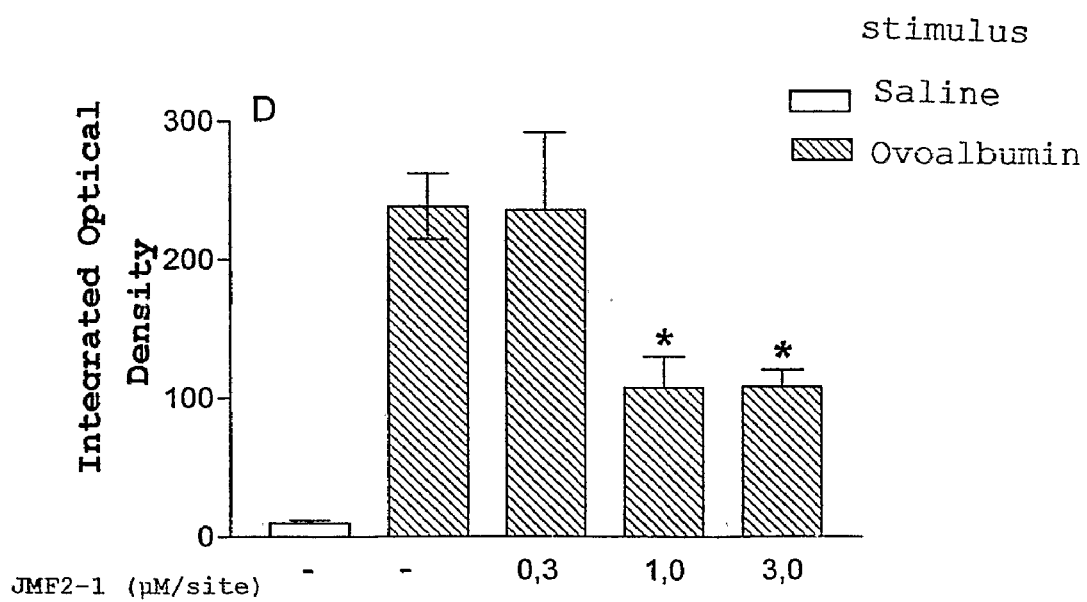

FIG. 4—Inhibitory effect of lidocaine and its derivatives in the inhibition of the vascular permeability increase caused by stimulation allergenic in rats.

Figure 5:
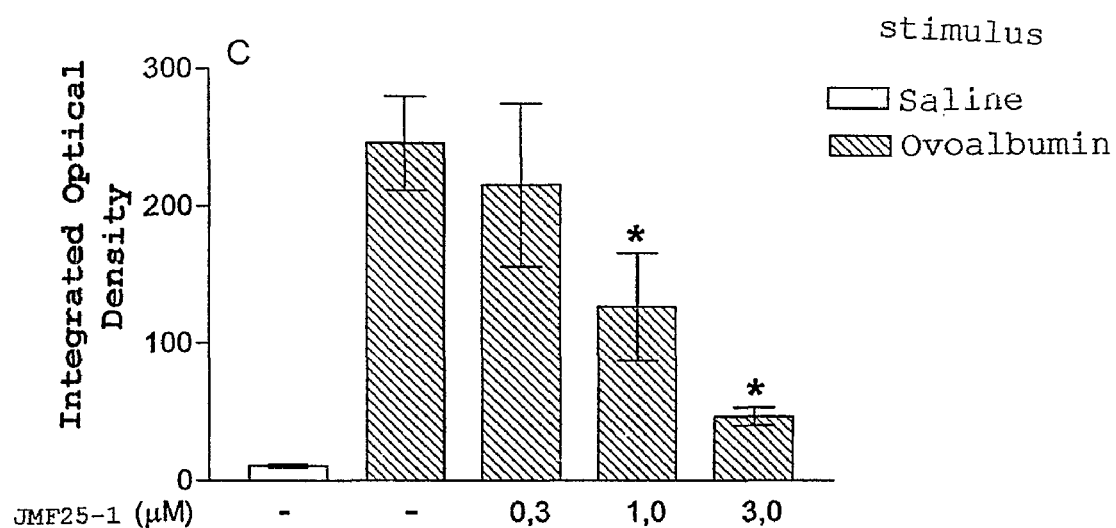

FIG. 5—Effect of JM24-1 derivative in the inhibition of the vascular permeability increase caused by stimulation allergenic in rats.

Figure 6:
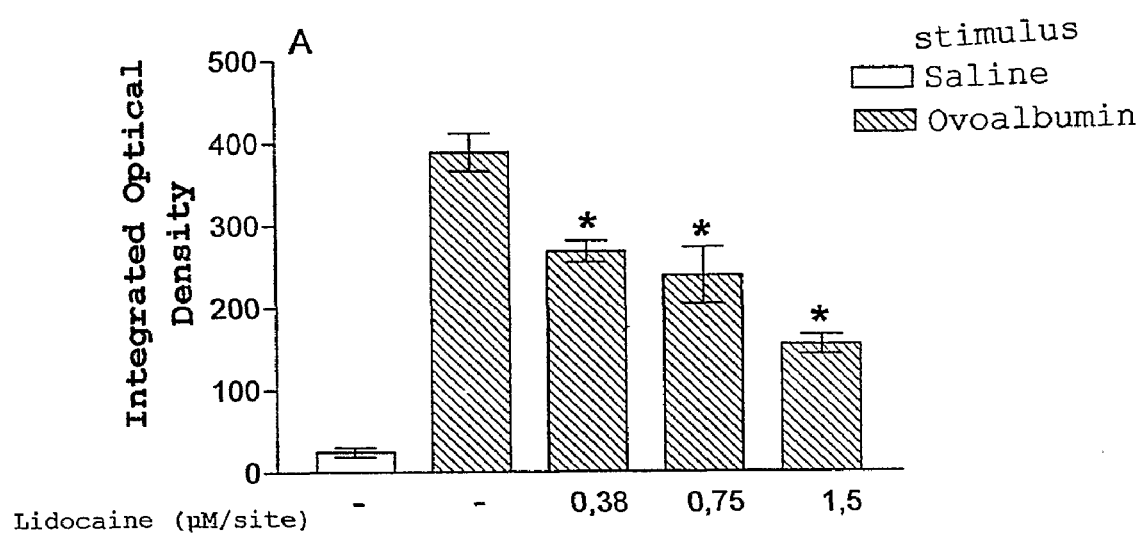

FIG. 6—Effect of JM25-1 derivative in the inhibition of the vascular permeability increase caused by stimulation allergenic in rats.

Figure 7:
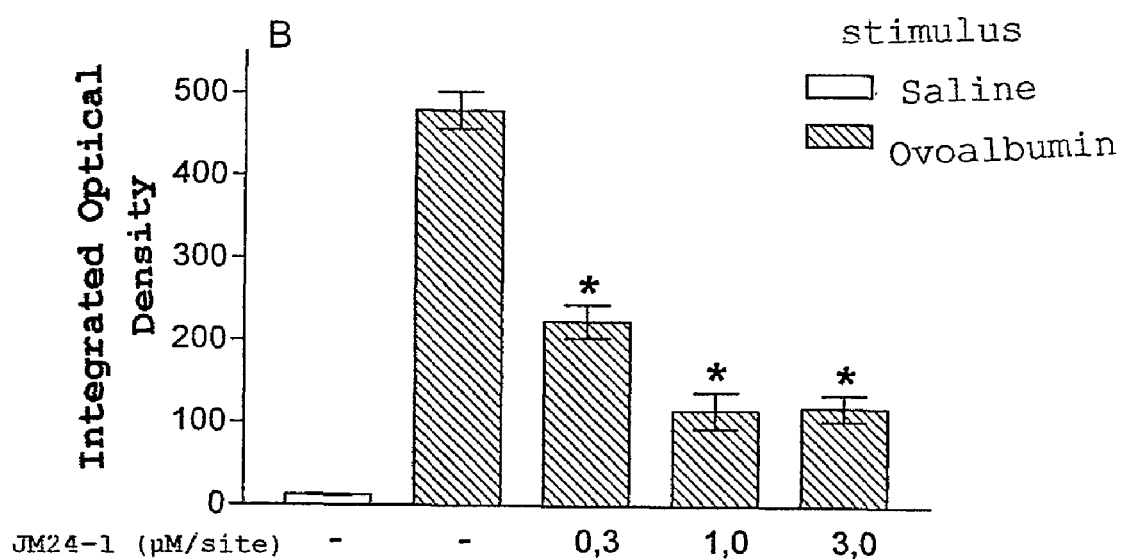

FIG. 7—Effect of JMF2-1 derivative in the inhibition of the vascular permeability increase caused by stimulation allergenic in rats.

Figure 8:
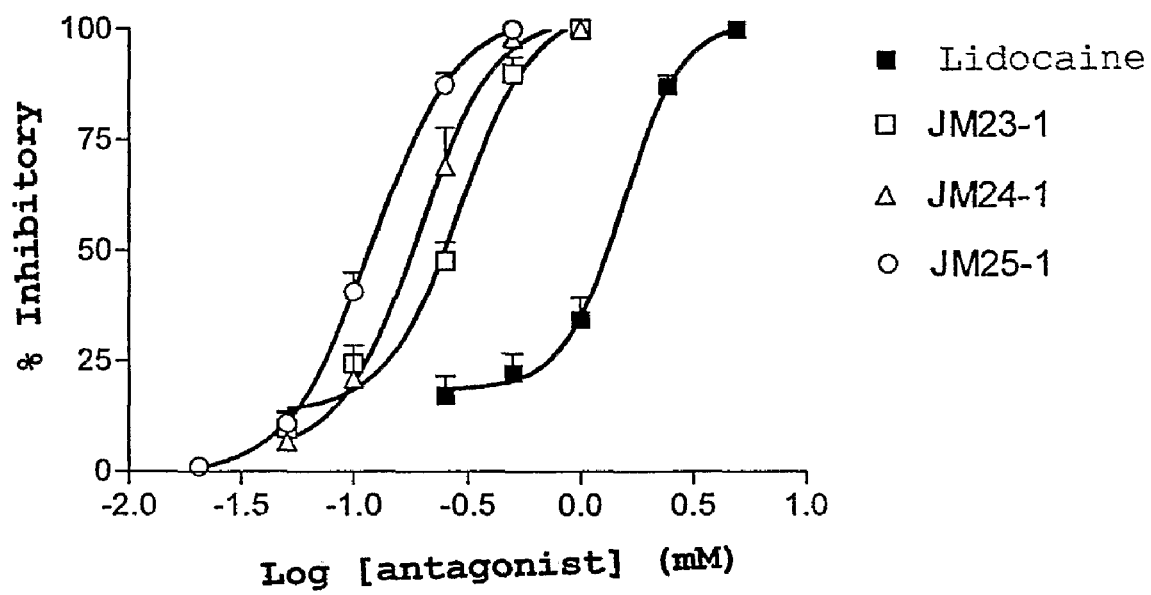

FIG. 8—Inhibitory effect of lidocaine and its derivatives in the inhibition of the anaphylactic contraction of intestinal non-striated muscle (ileum) in experimental animals induced by anaphylactic stimulation (Ovoalbumin.

Figure 9:
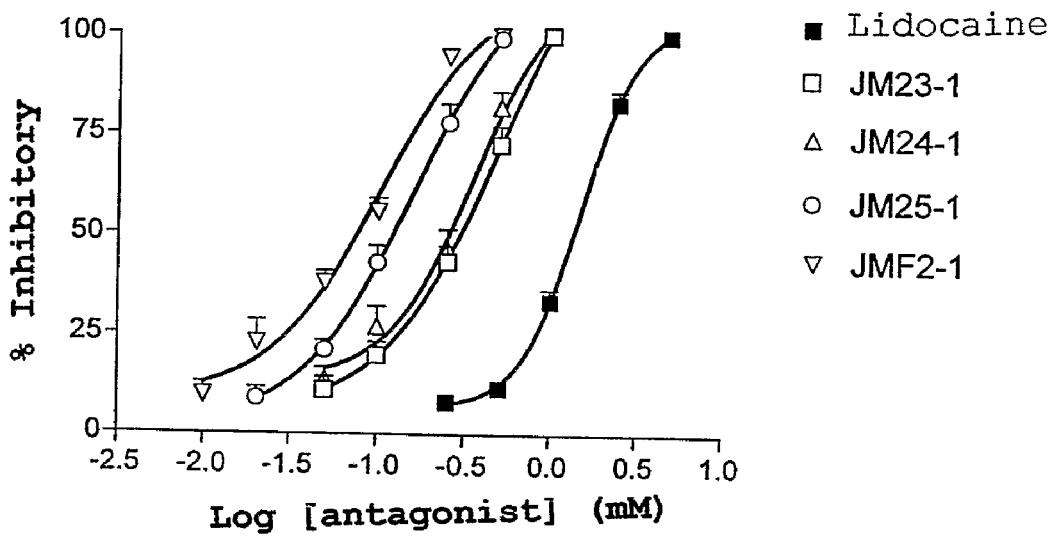

FIG. 9—Inhibitory effect of lidocaine and its derivatives in the inhibition of the contraction of intestinal non-striated muscle (ileum) induced by stimulation with histamine.

Figure 10:
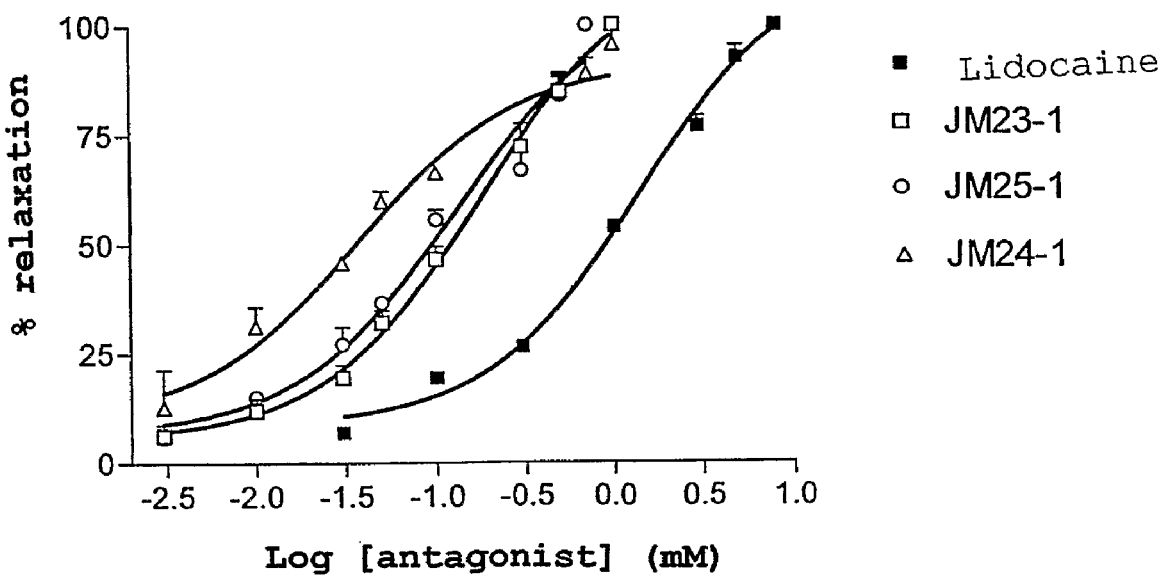

FIG. 10—Inhibitory effect of lidocaine and its derivatives in the induction of relaxing concentration-dependent of experimental animal pre-contracted trachea by anaphylatic stimulation.

Figure 11:
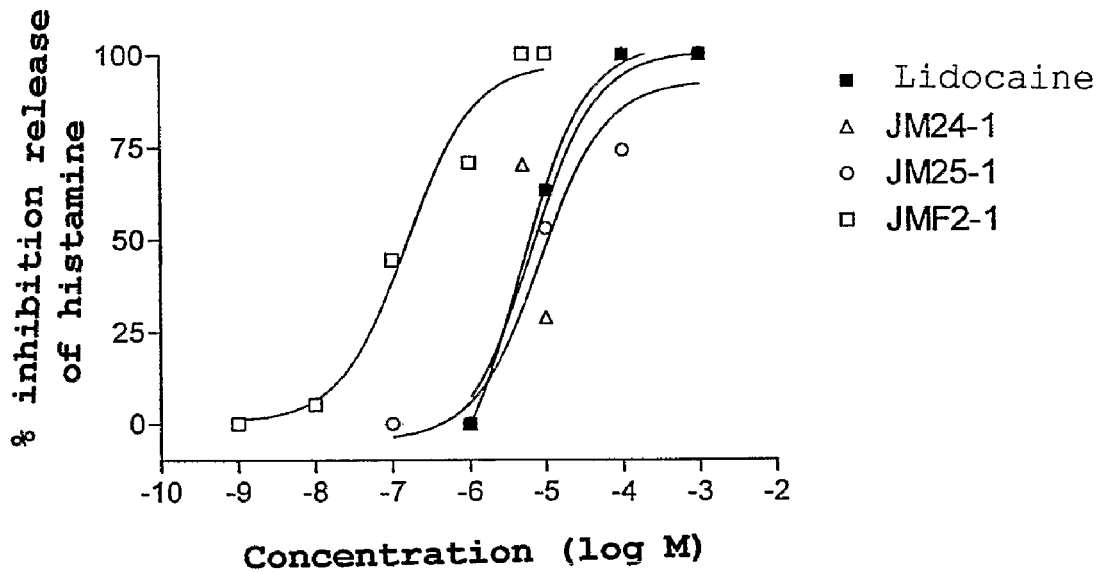

FIG. 11—Effect of lidocaine and its derivatives in the inhibition of the anaphylactic release of histamine by fragments of rats dorsal subcutaneous tissue.

Figure 12:
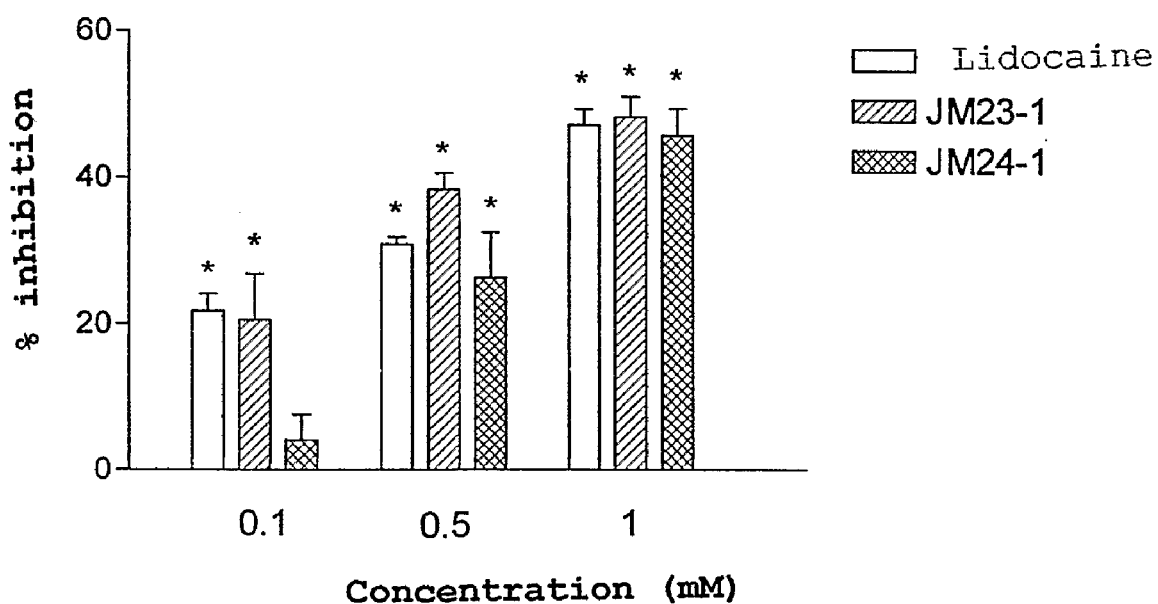

FIG. 12—Effect of lidocaine and its derivatives in the increase of citosolic calcium concentration after stimulation of eosinophils of rats with PAF (Platelet Activating Factor).

Figure 13:
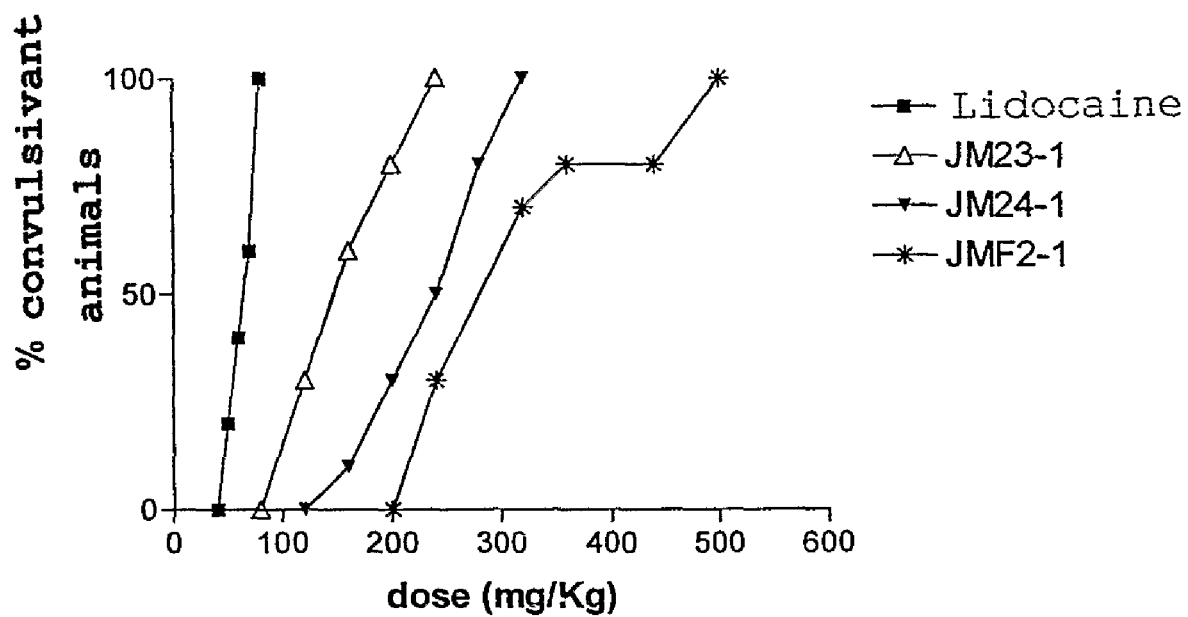

FIG. 13—Comparative evaluation of pro-convulsivant activity of lidocaine and its derivatives, injected through intraperitonial in Swiss 44 mice.

EXAMPLES

The present invention is described in details throughout examples presented bellow. It is necessary to highlight that the invention is not restricted to these examples, but it also comprises variations and modifications within the limits in which it works.

Example 1

Comparative Analisis of the Anesthetic Activity of Lidocaine and its Derivatives Method and Evaluation A. Animals Female and male Wistar rats, weighing between 200 and 250 g, they came from Oswaldo Cruz Foundation's Center of Laboratory Animal Raising were used. The procedures involving the animals were examined and approved by Oswaldo Cruz Foundation's Committee of Animal Ethics (CEUA-FIOCRUZ, License number 00085-02).

B. Local Anesthetic Activity

After brief anesthesia by exposure to the atmosphere enriched with dyethil ether, the animals were trichotomized dorsal region, where the intradérmicas injections with substances for test were performed; doses varied from 0.5 to 4

μMol/site, and vehicle (NaCl 0.9%) (negative control), the final volume was 50 μl. Each animal took six injections and four animals were used for each tested substance. The application points were mechanically estimulated with a tweezer in order to evaluate the integrity of sensitiveness. The site was considered not to be anesthesized whenever after the mechanical stimulation it was observed a local retraction of the skin, according to what had been previously reported. The evaluations began 10 minutes after intradermal injections had been taken, which continued every five minutes until it was obtained the cutaneous retraction response. The values (average±standard error of the mean, SEM) were expressed in terms of "Time of Anesthesia" in minutes.

Results

Administered in doses from 0.5 to 4 μMol/site, lidocaine derivatives identified as JM23-1, JM24-1, JM25-1 and JMF2-1 presented time of anesthesia significantly inferior to that one evidenced by lidocaine (FIG. 1). These molecules were selected among a plurality of lidocaine derivatives selected based on low anesthetic activity criteria and absence of signs of behavior alteration, including shivering, convulsion and prostration (data not shown). It is highlighted the minimization of the anesthetic effect of the derivative JMF2-1, which, in its higher dose (4 μMol/site), remained active for 28±1 min (n=4) at most, while lidocaine anesthesized the site for 168±3 min (n=4). The ranking of anesthetic potency for the tested molecules was:

lidocaine >>JM24-1>JM25-1>JM23-1>JMF2-1.

Through FIG. 1 it is observed that the local anesthetic effect of lidocaine and its derivatives evaluated in cutaneous sites of the dorsal area of adult Wistar rats, according to experiment previously established. The values, expressed in terms of "Time of Anesthesia" in minutes, are presented as the average±SEM of a minimum of 4 animals. Some SEM bars are not shown in the graph because they are lower than the group representative symbol. In each dose, varying from 0.5 to 4 μMol/site, the values obtained after the application of derivatives were statistically compared to those evidenced after lidocaine injection in the respective doses. Lidocaine derivatives presented times of anesthesia significantly inferior to the same as to lidocaine in all studied doses.

Example 2

Tonic Blockade of Na⁻ Currents in $GH_3$ by Lidocaine, JM24-1 and JMF2-1

Method and Avaliation

Rat clonal pituitary $GH_3$ cells were cultured in RPMI 1640 medium containing 10% fetal calf serum, penicillin (100 U/ml) and streptomycin (100 μg/ml), and plated on a glass sheet at 37° C. in a 5% $CO_2$ humidified atmosphere to be used within 1-2 days. Ion channel currents were recorded by means of a patch clamp technique. The cells cultured on the cover glass were placed in a chamber fixed to a microscope stage and continuously perfused with extracellular Saline (A) solution (in mM); 150 NaCl, 5 KCl, 1 $MgCl_2$, 0.01 $CaCl_2$, 1 EGTA, 10 HEPES, 2 $BaCl_2$, 0.1 $CdCl_2$, pH 7.4 at room temperature (22-25° C.) adjusted with NaOH. The cells were observed using phase contrast mode under an inverted microscope (Axiovert 100, Carl Zeiss, Oberkochem, D Germany). Tight-seal (>10 GΩ) whole cell voltage-clamp recordings were performed with an Axopatch-1D amplifier (Axon Instruments, San Mateo, Calif.). $Na^+$ currents were recorded in presence or absence of antagonists (lidocaine, JM24-1 or JMF2-1). Series resistance was 6-10 MΩ for all experiments when a pipette was filled with an intracellular Saline (B) solution in (mM); 150 KCl, 5 NaCl, 1 $MgCl_2$, 10 HEPES and 0.1 EGTA, pH 7.4 adjusted with NaOH. Fifteen minutes after rupture of the patch membrane, we started to record ion channel currents. Pulse protocols and data acquisition were controlled by Digidata 1320 interface (Axon Instruments, Palo Alto, Calif.), and acquired on a personal computer using Clampex 9 software. The $Na^+$ current recordings were filtered at 1 kHz and sampled at 8 kHz. About 26% of series resistance was electronically compensated. Drugs were applied to the recording chamber by gravity. Perfusion rate was maintained at 0.8-1.1 ml/min and bath volume was of 50 μl.

Results

Here we wanted to assess comparatively the effectiveness of lidocaine, JM24-1 and JMF2-1 on $Na^+$ current blockade by patch-clamp recording of $GH_3$ cells. Voltage-gated $Na^+$ currents were recorded from these cells in the presence or absence of treatment. In control experiments (n=6), $GH_3$ cells were depolarized from a holding potential −80 mV to +60 mV step pulse (2 s duration) leading to inward $Na^-$ currents (data not shown). Marked blockade of $Na^+$ currents were noted following treatment with increasing concentrations of lidocaine ($IC_{50}$ value=0.18 mM) as expected (FIG. 2, symbol ○). Remarkably, treatment with either JM24-1 (FIG. 2, symbol ●) or JMF2-1 (FIG. 2, symbol ▲) inhibited $Na^+$ currents in $GH_3$ but the concentrations required were significantly higher. Actually, the 50% inhibitory concentrations of JM24-1 and JMF2-1 were found to be 29 and 169 times higher than that noted in the case of lidocaine (5.2 and 25.4 mM, respectively), consistent with their reduced anaesthetic activity (FIG. 1)

Example 3

Lidocaine and its Derivatives Inhibit the Pulmonary Eosinophil Infitrate Caused by Allergenic Stimulation in Experimental Animals Method and Evaluation A. Animals, Sensitization and Challenge Female and male experimental animals were used, weighing between 300 and 400 g, they came from Oswaldo Cruz Foundation's Center of Laboratory Animal Raising. The procedures involving the animals were examined and approved by Oswaldo Cruz Foundation's Committee of Animal Ethics (CEUA-FIOCRUZ, License number 00085-02). The animals were sensitized through a cutaneous injection of a mixture with 50 μg ovoalbumin and 5 mg Al(OH)3, and challenged with ovoalbumin (1%) aerosol for 30 min 14 days afterwards, according to what was previously described. In order to avoid death of animals by anaphylatic asphyxia, all of them were treated intraperitonially with the anti-histaminic difenidramine (30 mg/kg) 30 minutes before being challenged.

B. Experimental Groups and Treatment

Five experimental groups were studied, with 7 animals each, including:

i) Negative group control, in which sensitized animals received sterile saline (NaCl, 0.9%) aerosol for 30 minutes on the 14$^{th}$ day;

ii) Positive group control, in which sensitized animals received aerosol de ovoalbumin (1%) diluted with saline for 30 minutes on the 14$^{th}$ day;

iii) Lidocaine group, in which sensitized animals received aerosol de ovoalbumin (1%) along with lidocaine (5%) for 30 minutes on the 14$^{th}$ day. These animals received 3 new aerolizations only with lidocaine (5%, 30 min) every 3 h;

iv) JM24-1 group, in which sensitized animals received aerosol de ovoalbumin (1%) along with lidocaine (5%) for 30 minutes on the 14$^{th}$ day. These animals received 3 new aerolizations only with JM24-1 (5%, 30 min) every 3 h;

iv) JMF2-1 group, in which sensitized animals received aerosol de ovoalbumin (1%) along with lidocaine (5%) for 30 minutes on the 14$^{th}$ day. These animals received 3 new aerolizations only with JMF2-1 (5%, 30 min) every 3 h;

C. Bronchoalveolar Lavage and Eosinophils Counting

All the animals were anesthesized terminally through an intraperitonial injection of pentobarbital (200 mg/kg) 24 h after the antigenic challenge, to wash the bronchoalveolar space according to the techniques previously described. Total leukocyte count were done after dilution of bronchoalveolar lavage samples in Turk liquid and counting in the Neubauer chamber with the assistance of direct-light microscopy. The differential eosinophil count was done also under direct-light microscopy, after centrifugation of samples of the lavage as well as its exposure to specific dyestuff (May-Grunwald-Giemsa dye).

D. Statistical Analisis

The averages± standard error of the mean of the groups investigated were analyzed based on statistics through the test of variance analysis (ANOVA), followed by the Newman-Keuls-Student test. The P values inferior or equal to 0.05 were considered to be significant.

Results

As shown in FIG. 3, the accumulation of eosinophils in the bronchoalveolar area of sensitized experimental animals after allergenic challenge was clearly sensitive to lidocaine treatment. These data confirm in vivo previous results obtained in studies in vitro in which it was shown that lidocaine is able to induce human eosinophils to death by inducing apoptose. FIG. 2 illustrates also the supressig effect of the derivatives JM24-1 and JMF2-1, supporting the proposition that the anti-inflammatory activity of the anesthetics lidocaine remains intact in these molecules. The derivatives JM24-1 and JMF2-1 are equipotent to lidocaine in terms of blocking the accumulation of eosinophils in the bronchoalveolar area of sensitized experimental animals after allergenic challenge.

In FIG. 3 it is observed the inhibitory effect of lidocaine and its derivatives upon pulmonary eosinophilia caused by allergenic stimulation in experimental animals. Values, expressed in terms of "number of eosinophils×10$^6$/lavage" are presented as average±SEM in at least 7 animals. In the negative control group, animals previously sensitized were artificially-challenged through exposure to sterile saline (NaCl, 0.9%) aerosol. In the positive group control, sensitized animals were challenged with ovoalbumin 1% aerosol but did not get any treatment. In the groups treated with lidocaine, JM24-1 or JMF2-1, the animals received ovoalbumin 1% aerosol along with lidocaine or test similar at 5% concentration besides other 3 aerosolizations every 3 h. "+" represents the difference statistically significant (P<0.05), when positive and negative controls, were compared. "*" represents the difference statistically significant (P<0.05), when the group treated and the positive control group were compared. Lidocaine, JM24-1 and JMF2-1 were equipotent to block the influx of eosinophils induced by antigen.

Example 4

Lidocaine and its Derivatives Inhibit the Vascular Permeability Increase Caused by Allergenic Stimulation in Rats Method and Evaluation A. Animals and Sensitization Protocol Male Wistar rats were used, weighing between 200 and 250 g, they came from Oswaldo Cruz Foundation's Center of Laboratory Animal Raising were used. The animals were kept under room temperature with free access to water and ration. The procedures involving the animals were examined and approved by Oswaldo Cruz Foundation's Committee of Animal Ethics (CEUA-FIOCRUZ, license number 00085-02). The animals were sensitized by subcutaneous injection with a mixture of 50 μg ovoalbumin and 5 mg Al(OH)3 and challenged intradermally 14 days afterwards.

B. Experimental Groups, Treated and Antigenic Challenged

The animals were anesthesized in an atmosphere enriched with dyetil-ether and had their dorsal region trichotomized before being intradermally injected in different sites, with saline and increasing concentrations of lidocaine or derivatives in a total volume 50 μl/site. Four experimental groups were studied with four animals each:

I. Lidocaine group, receiving intradermal injections of saline and lidocaine (0.38-1.5 μMol/site);

II. JM24-1 group, receiving intradermal injections of saline and JM24-1 (0.3-3 μMol/site);

III. JM25-1 group, receiving intradermal injections of saline and JM25-1 (0.3-3 μMol/site);

IV. JMF2-1 group, receiving intradermal injections of saline and JMF2-1 (0.3-3 μMol/site).

Ten minutes after the first application of test substances, the animals were anesthetized again in a dyetil-ether chamber for intravenous administration of Evans blue vital dye (25 mg/Kg) for the marking of plasmatic overflow in the sinus-venosus penis. 15 minutes past the Evans blue application, the sites previously stimulated with saline or test substances were now stimulated with ovoalbumin (3 μg/site) or vehicle (NaCl, 0.9%), in a final volume final of 20 μl.

C. Response Quantifying

Thirty minutes after the antigenic challenge, the animals were sacrificed in an atmosphere rich in $CO_2$, having their dorsal skin removed to have the intensity of plasmatic overflow evaluated based on the area and intensity of the overflowed dye. The magnitude of the responses in each site was measured after digitalization of overflowing points on the cutaneous inner face, through the use of a scanner (make HP, model ScanJet 4c) and image analysis (Image Pro Plus, version 4.5.1, Media Cybernetics, USA). The quantified parameter was the integrated optical density integrada (IOD)—which is precisely the product of the area divided by the average blue in the analyzed site.

D. Statistical Analysis

The results obtained in different experimental groups were expressed as average± standard error of the mean and statistically analyzed through the test of variance analysis (ANOVA), followed by the Newman-Keuls-Student test. The "P" values inferior or equal to 0.05 were considered to be significant.

Results

The intradermal injection of ovoalbumin (3 μg/site) caused intense response to plasmatic overflow which was inhibited by lidocaine (0.19-3 μMol/site) in a proportional manner to the applied dose (FIG. 4). The derivatives JM24-1 (FIG. 5), JM25-1 (FIG. 6) and JMF2-1 (FIG. 7) were also capable of inhibit the plasmatic overflow caused by antigenic stimulation, in dose and effectiveness comparable to those observed after the topic treatment with lidocaine. Theses results indicate that the derivatives studied hold the lidocaine capacity to block the increase of vascular permeability and the plasmatic overflow induced by allergic stimulation.

In FIGS. 4 and 7 are shown the effects of lidocaine and its derivatives on the inhibition of the vascular permeability increase caused by allergenic stimulation in rats. The values, expressed in terms of Integrated Optical Density (IOD), are shown as average±SEM with at least 4 animals. The animals received intradermal injections, in different sites, of sterile saline (NaCl, 0.9%), lidocaine (0.38-1.5 μMol/site) or similar (0.3-3.0 μMol/site). The symbols (+) e (*) represent statistically significant differences (P<0.05) when compared to the negative and positive group controls, respectively. In the inhibition of the vascular permeability increase the similar JM24-1, JM25-1 and JMF2-1 were equipotent to lidocaine.

Example 5

Lidocaine and its Derivatives Inhibit the Anaphylactic Contraction of the Non-striated Intestinal Muscle (Ileum) of Sensitized Experimental Animals Method and Evaluation
A. Animals, Sensitization and Preparation of Target Tissue
Female and male experimental animals were used, weighing between 300 and 400 g, they came from Oswaldo Cruz Foundation's Center of Laboratory Animal Raising. The procedures involving the animals were examined and approved by Oswaldo Cruz Foundation's Committee of Animal Ethics (CEUA-FIOCRUZ, Licenca no. 00085-02). The animals were sensitized through a subcutaneous injection with a mixture of 50 μg ovoalbumin and 5 mg $Al(OH)_3$. From fourteen to thirty days after the sensitization, the experimental, animal was sacrificed in a chamber of carbonic gas to have its abdomen open and the location of the ileocecal valve. At this point, the intestine was sectioned and a segment of the small intestine, about 20 cm (equivalent to the ileum) was carefully removed and internally washed with a warmed solution (37° C.) of Tyrode (Composition in mM) (NaCl 137; KCl 2.7; $NaH_2PO_4$ 0.42; $NaHCO_3$ 11.9; $MgCl_2$ 0.5; $CaCl_2$ 1.8; glucose 5.6) to remove the fecal content. In the experiments over the study of the effects of lidocaine and similars on non-anaphylactic contraction (contraction by histamine) non-sensitized experimental animals were used.
B. Measure of Contraction and Treatments
About 3-cm ileum fragments were vertically mounted in 10 ml glass cuvettes, immersed in Tyrode's solution at 37° C., aerated with carbogen ($O_2$, 95% and $CO_2$, 5%) and supplemented with atropine according to the standard procedure. The tissue had one of its ends tied to a rod while the other end was coupled with a transductor after the transference from the rod to the cuvette. The contractions were isotonically registered (basal tension of 1 g) with the support of a transductor of displacement-force connected to a computerized system to capture data. After a 30 minute period of balance, each segment was repeatedly stimulated by histamine (1 μM) until response stabilization. To induce anaphylatic contraction, ileum segments from sensitized experimental animals were stimulated by ovoalbumin (10 μg/ml). In the experiments carried out in order to test the inhibitory contracting activity, the stimulation of tissues by ovoalbumin (10 μg/ml) or histamine (5 μM) ocorred in a regime of co-incubation with lidocaine or its derivatives added to the nourishing solution 10 minutes before. The results were presented as a percentage of inhibition calculated in relation to the contractive effect obtained from stimulated and non-treated preparations.
C—Statistical Analysis
Concentration-response data were adjusted through non-linear regression curves with the assistence of a graphics software (GraphPad Prism, USA). The concentration of an antagonist needed to inhibit the contractive response to inhibit the contractive response after stimulation by histamine or antigen at 50% (IC50) was used to compare the anti-spasmodic potency. The values expressed as an average ± standard error of the mean and statistically analysed through the test of analysis variance (ANOVA), followed by the Newman-Keuls-Student test. The "P" values inferior or equal to 0.05 were considered significant.

Results
The results showed that the treatment with lidocaine inhibited the way concentration-response dependent the contraction of the isolated ileum of na experimental animal induced by antigen (FIG. 8) and histamine (FIG. 9), with values of IC50 of 1.43±0.09 mM and 1.41±0.12 mM, respectively. The results showed also the major sensitivity to the treatment with lidocaine derivatives, so that in case of anaphylactic contraction (FIG. 8) as in the case of contraction provoked by histamine (FIG. 9). These results clearly indicate that the anesthetic activity is not only relevant to the anti-spasmodic effect of lidocaine. They indicate also that the derivatives studied revealed significantly more potent than lidocaine in this system. Based on IC50 values presented in Table 1, the potency ranking of the test substances to block the anaphylactic contraction was: JM25-1>JM24-1>JM23-1>lidocaine.

TABLE 1

Concentration of lidocaine and its derivatives necessary to inhibit 50% (IC50) of the contractive response of the isolated ileum of an experimental animal induced by antigen (10 μg/ml) or histamine (5 μM).

| Compounds | Stimulation with antigen IC50 (mM) | Stimulation with histamine IC50 (mM) |
|---|---|---|
| Lidocaine | 1.43 ± 0.09 | 1.41 ± 0.12 |
| JM23-1 | 0.33 ± 0.00* | 0.38 ± 0.06* |
| JM24-1 | 0.19 ± 0.04* | 0.31 ± 0.06* |
| JM25-1 | 0.12 ± 0.01* | 0.14 ± 0.02* |
| JMF2-1 | — | 0.10 ± 0.01* |

The values represent the average ±SEM obtained from at least 3 animals.
The asterisk represents the difference statistically significant (P < 0.05), when compared to a lidocaine group.

The values represent the average±SEM obtained from at least 3 animals. The asterisk represent the difference statistically significant (P<0.05), when compared to a lidocaine group.

In FIG. 8 there is a co-incubation with lidocaine or its derivatives inhibiting in a concentration-dependent manner to a contraction of the isolated ileum of an experimental animal induced by anaphylactic stimulation (Ovoalbumin, 10 μg/ml). The values represent the average±SEM of inhibited percentages of at least 3 animals.

While, in FIG. 9 there is a co-incubation with lidocaine or its derivatives inhibiting in a manner concentration-dependent the isolated ileum contraction of the experimental animal induced by histamine stimulation (5 μM). The values represent the average±SEM of the inhibiting percentages of at least 3 animals.

Example 6

Lidocaine and its Derivatives Induce Relaxation of the Experimental Animal Pre-contracted Trachea by Anaphylactic Stimulation Method and Evaluation
A. Animals, Sensitization and Tissue Preparation
Female and male experimental animals were used, weighing between 300 and 400 g, they came from Oswaldo Cruz Foundation's Center of Laboratory Animal Raising. The procedures involving the animals were examined and approved by Oswaldo Cruz Foundation's Committee of Animal Ethics (CEUA-FIOCRUZ, License number 00085-02). The animals were sensitized through a subcutaneous injection with a mixture of 50 μg ovoalbumin and 5 mg Al(OH)3. Fourteen to thirty days after the sensitization, the experimental animal was sacrificed in a chamber of carbonic gas to have its trachea removed. The trachea was transferred to a Petri dish containing Krebs solution (composition in mM) (NaCl—119; KCl—4.7; NaH2PO4—1.2; NaHCO3—25; MgCl2—1.2, CaCl2—2.5, and glucose—11.5). The total segment was divided into fragments of about 3 to 4 rings that were sectioned at the extreme ending, the muscular part of the trachea.

B. Mouting the Preparation, Measure of Contraction and Treatments

Each fragment had one of its ends tied to a rod while the other end was connected to an isometric transductor (U Basile, Italy) after the transference from the rod to a 10 ml glass cuvette. The tissue was maintained immersed in Krebs solution at 37° C. aerated with carbogen (O2, 95% and CO2, 5%). The contractions were registered with the assistence of a computerized system of data capture (Letica, Spain). After a 30 minute period of balance, each segment was pre-contracted with ovoalbumin (20 μg/ml) in order to produce concentration-response curves of relaxation with lidocaine and its derivatives. The results were shown as a percentage of relaxation in relation to the plateau of the anaphylatic pre-contraction.

C—Statistical Analysis

Concentration-response data were adjusted through non-linear regression curves with the assistence of a graphics software (GraphPad Prism, USA). The concentration of an antagonist needed to obtain a relaxation at a rate of 50% pre-contraction plateau (IC50) was used to compare the spasmolytic potency. The values were expressed as an average± standard error of the mean and statistically analysed through the test of analysis variance (ANOVA), followed by the Newman-Keuls-Student test. The "P" values inferior or equal to 0.05 were considered significant.

Results

Confirming a former study, the results showed (FIG. 10) that lidocaine was able to induce a concentration-response relaxation dependent to the pre-contracted trachea by anaphylatic stimulation, with value IC50 equal to 1.35±0.02 (average±SEM) (N=3) (Table 2). The FIG. 9 shows once again that lidocaine derivatives JM23-1, JM24-1 e JM25-1 were more potent than lidocaine itself now to revert spasm caused by antigenic stimulation. As indicated in table 2, compared to IC50 lidocaine, the IC50 values of the derivatives are shown significantly lower reaching reductions at the rate 6 to 45 times, evidencing major sensitivity of anaphylatic spasm to these derivatives. Based on the IC50 values presented, the ranking of potency of the test substances in this system was: JM24-1>JM25-1>JM23-1>lidocaine.

TABLE 2

Concentration values of lidocaine and its derivatives necessary to relax in 50% (IC50) the anaphylatic spasm of the experimental animal trachea.

| Compounds | IC50 (mM) |
|---|---|
| Lidocaine | 1.35 ± 0.02 |
| JM23-1 | 0.22 ± 0.06* |
| JM24-1 | 0.03 ± 0.00* |
| JM25-1 | 0.13 ± 0.02* |

The values represent the average±SEM obtained from at least 3 animals. The asterisk represents the differenced statistically significant (P<0.05) when compared to the lidocaine group.

Example 7

Lidocaine and its Derivatives Inhibit the Anaphylactic Release of Histamine by Fragments of Dorsal Subcutaneous Tissue of Rats Method and Evaluation A. Animals, Sensitization and Tissue Preparation Female and male Wistar rats were used, weighing between 180 and 200 g, they came from Oswaldo Cruz Foundation's Center of Laboratory Animal Raising. The procedures involving the animals were examined and approved by Oswaldo Cruz Foundation's Committee of Animal Ethics (CEUA-FIOCRUZ, Port. 00085-02). The rats were sensitized with a subcutaneous injection containing a mixture of 50 μg oval-bumina plus 5 mg Al(OH)$_3$. Fourteen days after the sensitization the animals were sacrificed in a chamber of $CO_2$, to have their dorsal hypodermis removed which was fragmented into smaller segments of about 3 mm in a Petri dish containing PBS. The fragments were individually transferred to a dish with 48 pools containing 500 μl of Hanks with $Ca^{++}$ and $Mg^{++}$.

Five experimental groups were studied in quadruplicates:

I. Saline group, negative control, pools where the tissue was neither treated nor stimulated;

II. Ovoalbumin group, positive control, pools where the tissue was not treated but it was stimulated by ovoalbumin (300 μg/ml);

III. JM24-1 group, pools where the tissue was previously treated with JM24-1 before the stimulation with ovoalbumin (300 μg/ml);

IV. JM25-1 group, pools where the tissue was previously treated with JM25-1 before the stimulation with ovoalbumin (300 μg/ml);

V. JMF2-1 group, pools where the tissue was previously treated with JMF2-1 before the stimulation with ovoalbumin (300 μg/ml).

Treated and non-treated pools were kept at 37° C. in a metabolic incubator (atmosphere containing 95% $O_2$ and 5% $CO_2$) for 60 minutes before the antigenic challenge. After the addition of ovoalbumin (300 μg/ml) all the pools were incubated again in a metabolic oven for more than 60 minutes. After removal of tissue for drying and weighing, the culture medium was collected and acidified with perchloric acid 0.4 N being, after centrifugation 150×g for 10 min. stocked at −20° C. until the moment of fluorimetric quantifying of histamine, according to the previous work. The values were shown like nanograms of released histamine by mg of tissue (dry weight).

Results

The results confirmed previous data in which the inhibitory effect of lidocaine over the anaphylactic release of histamine was encountered after system activation of the IgE-mast cell. It was shown that the derivatives JM24-1 and JM25-1 were also capable of releasing histamine in concentrations comparable to that of lidocaine, while JMF2-1 revealed to be about 29 times more potent in this system (FIG. 11). The derivative JM23-1 also tested was inactive (data not-shown). Based on data of IC50 presented in table 3, the ranking of potency of inhibitory activity of histamine release of studied active molecules was: JMF2-1>lidocaine>JM24-1>JM25-1.

FIG. 11 shows the effect of treatment with lidocaine, JM24-1, JM25-1 and JMF2-1 over anaphylactic release of histamine originated from dorsal subcutaneous tissue of rats actively sensitized.

TABLE 3

Values of lidocaine concentration and its derivatives necessary to inhibit in 50% (IC50) the histamine release caused by anaphylatic stimulus of the subcutaneous tissue of rats.

| Compounds | IC50 (µM) |
|---|---|
| Lidocaine | 4.50 |
| JM24-1 | 6.46 |
| JM25-1 | 8.35 |
| JMF2-1 | 0.16 |

Example 8

Effect of Lidocaine and its Derivatives Over Calcium Influx in Eosinophils of Rats Method and Evaluation
A. Animals Female and male Wistar rats were used, weighing between 200 and 250 g, they came from Oswaldo Cruz Foundation's Center of Laboratory Animal Raising. The procedures involving the animals were examined and approved by Oswaldo Cruz Foundation's Committee of Animal Ethics (CEUA-FIOCRUZ, Licenca no. 00085-02).

B. Eosinophils Isolation

The animals were sacrificed in a chamber of $CO_2$ and a population of cells containing 10-15% eosinophils were recovered from the peritoneal cavity after washing the same with 20 ml Hanks, as previously described. After centrifugation, the cellular sediment was resuspended and the leukocytes subtypes (mononuclear cells, eosinophils and mast cells) separated in a discontinuous gradient of Percoll (double layer) centrifugated at 400×g for 25 minutes. The eosinophils (85-95% purity) were recovered in the interface 56%-72%, washed in RPMi medium to eliminate residue of Percoll and related. The total cells isolated was obtained after the dilution of a sample in Türk liquid and couting in Neubauer chamber with the assistance of direct-light microscopy. The populational purity analysis was done by direct-light microscopy in cytocentrifugates dyed with May-Grunwald-Giemsa.

C. Measure of Citosolic Calcium in Purified Eosinophils

The eosinophils ($1 \times 10^7$/ml) were loaded with 3 µM Fura 2-AM as described, washed in PBS enriched with 0.1% BSA, and resuspended in a final concentration of $0.5 \times 10^6$/ml PBS containing 0.25% BSA, HEPES and glucose (10 nM). Alíquotas de células (1.5 ml) were dispensed in quartz cuvettes and balanced with 1 mM calcium at 37° C. for 10 minutes before being used. Fluorescence changes were measured by fluorometer Shimatzu (model RF 1501) as previously described. The calculus of free calcium was derived from the fluorescence spectrum (wave length of excitation, 340 and 380 nm; emission 510 nm) according to the method established. The values were represented as percentage of inhibition in relation to group control.

Three experimental groups were studied:

I. Group control, in which eosinophils previously loaded with Fura 2-AM were stimulated with the platelet activating factor (PAF) (1 µM) for the measure of calcium transient.

II. JM23-1 group, in which eosinophils previously loaded with Fura 2-AM were incubated with increasing doses of JM23-1 for 5 minutes before being stimulated by PAF (1 µM) for the measure of calcium transient.

III. Grupo JM24-1, in which eosinophils previously loaded with Fura 2-AM were incubated with increasing doses of JM23-1 for 5 minutes before being stimulated by PAF (1 µM) for the measure of calcium transient.

D—Statistical Analysis

The values were expressed as an average± standard error of the mean and statistically analyzed through the test of variance analysis (ANOVA), followed by the Newman-Keuls-Student test. The "P" values inferior or equal to 0.05 were considered to be significant.

Results

As illustrated by FIG. 12, lidocaine (0.1 at 1 mM) inhibited the concentration-dependent manner of the increase of citosolic calcium in eosinophils stimulated by PAF (1 µM), reaching a blocking of 47±2% (Average±SEM) (n=8) in the highest concentration. FIG. 12 also shows that the derivative JM23-1 was equipotent to lidocaine in this system and that, although less effective in lower concentrations, the similar JM24-1 was so effective as lidocaine and JM23-1 in higher concentrations.

Therefore, in the system of eosinophylic activation by PAF, evaluated by the increase in the concentration of citosolic calcium, the inhibitory potency ranking of the studied molecules was: lidocaine=JM23-1>JM24-1.

FIG. 12 shows the effect of lidocaine and its derivatives over the increase in the concentration of citosolic calcium after stimulation of eosinophils in rats with PAF. The values were expressed as an average±SEM of at least 4 different experiments. The asterisk represents statistical significancy (P<0.05) when compared to the non-treated group.

Example 9

Comparative Analysis of Convulsivant Activity of Lidocaine and its Derivatives

Method and Evaluation
A. Animals

Female and male Swiss 44 mice were used, weighing between 25 and 30 g, they came from Oswaldo Cruz Foundation's Center of Laboratory Animal Raising. The procedures involving the animals were examined and approved by Oswaldo Cruz Foundation's Committee of Animal Ethics (CEUA-FIOCRUZ, Act 00085-02).

B. Convulsive Atack

Groups of 10 animals had lidocaine injected via intraperitonial with, JM23-1, JM24-1 or JMF2-1 (40 to 500 mg/Kg) and were left in a plastic box for observation of the appearance of convulsive response. The percentage of animals which demonstrated characteristical signs of tonic-clonic convulsion in each group was determined after 15 minutes since the drug injection previously described. For each molecule, the necessary dose to induce a convulsive clinical Figure in 50% of the animals (DE50) was determined by linear regressive curves interpoled (GraphPad Prim, version 3.03).

Results

Considering the acknowledged potentiality of central toxic effect of local anesthetics, dose-response curves of lidocaine and three derivatives were determined in mice as an initial approach to the risk of a convulsive attack introduced by this molecules. Administered via intraperitonial at 40-500 mg/Kg doses, the molecules JM23-1, JM24-1 and JMF2-1 presented a convulsivant activity noticeably inferior to that one evidenced by lidocaine (FIG. 10). It is important to highlight that none of the similar substances were able to induce convulsion in mice in a dose of 80 mg/Kg, condition in which lidocaine led 100% of the injected animals to convulsion. The values of DE50 were 62, 154, 230 and 305 mg/kg to lidocaine, JM23-1, JM24-1 e JMF2-1 respectively.

Thus, the ranking of the convulsivant activity to the studied molecules was: Lidocaine>JM23-1>JM24-1>JMF2-1. In a whole, the results suggest a higher security margin for these derivatives of lidocaine.

In FIG. 13 it is shown a comparative evaluation of the pro-convulsivant activity of lidocaine and its derivatives, injected via intraperitonial in Swiss 44 mice. Ten animals were used for each administered dose.

The invention claimed is:

1. A METHOD OF TREATMENT comprising:
administering to a human being a therapeutically effective amount of a pharmaceutical composition comprising a lidocaine-derived compound of formula:

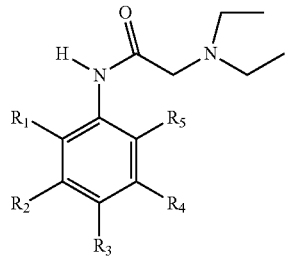

or a pharmaceutically acceptable salt thereof, wherein:
$R_1=R_2=CH_3$ and $R_3=R_4=R_5$ are H;
$R_1=R_3=CH_3$ and $R_2=R_4=R_5$ are H;
$R_1=R_4=CH_3$ and $R_2=R_3=R_5$ are H; or
$R_1=CF_3$ and $R_2=R_3=R_4=R_5$ are H;
in a pharmaceutically acceptable vehicle, wherein the lidocaine-derived compound has (i) anti-inflammatory activity and (ii) reduced anesthetic activity compared to lidocaine, and wherein the pharmaceutical composition is administered for the treatment of an atopic disease, non-atopic asthma, or chronic intestinal inflammation.

2. THE METHOD according to claim 1, wherein the pharmaceutical composition is in spray, solution, or emulsion form to be applied by nebulization.

3. THE METHOD according to claim 1, wherein the pharmaceutical composition is administered in a form for oral or injectable use.

4. THE METHOD according to claim 1, wherein the pharmaceutical composition administered to the human being who needs the referred treatment comprises a therapeutically effective amount of a lidocaine derived compound of formula:

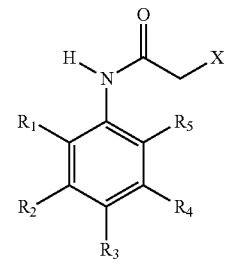

or a pharmaceutically acceptable salt thereof, wherein:
X is $N(CH_2CH_3)_2$;
$R_1$ is $CF_3$; and
$R_2=R_3=R_4=R_5$ are H;
in a pharmaceutically acceptable vehicle.

5. THE METHOD according to claim 4, wherein the pharmaceutical composition is in spray, solution, or emulsion form to be applied by nebulization.

6. THE METHOD according to claim 4, wherein the pharmaceutical composition is administered in a form for oral or injectable use.

7. THE METHOD according to claim 1, wherein the atopic disease is asthma, rhinitis, allergic urticaria, or chronic lung inflammation associated with eosinophilia.

8. THE METHOD according to claim 1, wherein the chronic intestinal inflammation is colitis.

9. THE METHOD according to claim 4, wherein the atopic disease is asthma, rhinitis, allergic urticaria, or chronic lung inflammation associated with eosinophilia.

10. THE METHOD according to claim 4, wherein the chronic intestinal inflammation is colitis.

* * * * *

UNITED STATES PATENT AND TRADEMARK OFFICE
CERTIFICATE OF CORRECTION

PATENT NO. : 8,163,803 B2
APPLICATION NO. : 11/570234
DATED : April 24, 2012
INVENTOR(S) : Martins et al.

It is certified that error appears in the above-identified patent and that said Letters Patent is hereby corrected as shown below:

In the Specification:

Column 2, line 4, "interferece" should read -- interference --.

Column 2, line 51, "recognized bring" should read -- recognized to bring --.

Column 3, line 2, "na" should read -- an --.

Column 3, line 18, "etc) e chemokines" should read -- etc.) and chemokines --.

Column 3, line 59, "however, individuals" should read -- however, in individuals --.

Column 3, line 65, "prevent from an" should read -- prevent an --.

Column 4, line 15, "inconvenients" should read -- inconveniences --.

Column 4, line 53, "(III) e" should read -- (III) and --.

Column 6, line 5, "(III) e (IV):" should read -- (III) and (IV): --.

Column 7, line 34, "intrinsec" should read -- intrinsic --.

Column 8, line 24, "(Ovoalbumin." should read -- (Ovalbumin). --.

Column 8, line 45, "bellow" should read -- below --.

Column 8, line 52, "Analisis" should read -- Analysis --.

Column 8, line 58, "they came from" should read -- from --.

Column 8, line 65-66, "trichotomized dorsal" should read -- trichotomized in the dorsal --.

Column 8, line 66, "intradérmicas" should read -- intradermal --.

Column 8, line 66, "test" should read -- testing --.

Column 9, line 1, "vehicule" should read -- vehicle --.

Column 9, line 4, "estimulated" should read -- stimulated --.

Column 9, line 30, "derivatives evaluated" should read -- derivatives were evaluated --.

Column 9, line 32, "experiment" should read -- experiments --.

Column 9, line 48, "Avaliation" should read -- Evaluation --.

Signed and Sealed this
Second Day of September, 2014

Michelle K. Lee
*Deputy Director of the United States Patent and Trademark Office*

Page 1 of 2

CERTIFICATE OF CORRECTION (continued)
U.S. Pat. No. 8,163,803 B2

Column 10, line 42, "they came from" should read -- from --.

Column 10, line 48, "A1(OH)3," should read -- Al(OH)$_3$ --.

Column 11, line 4, "iv)" should read -- v) --.

Column 11, line 33, "supressig" should read -- suppressing --.

Column 11, line 67, "they came from" should read -- from --.

Column 12, line 7, "A1(OH)3," should read -- Al(OH)$_3$ --.

Column 12, line 58, "inhibit" should read -- inhibiting --.

Column 13, line 4, "(+) e (*)" should read -- (+) and (*) --.

Column 13, line 20, "they came from" should read -- from --.

Column 13, line 55, "ovoalbumin" should read -- ovalbumin --.

Column 13, line 56, "ocorred" should read -- occurred --.

Column 13, lines 65-66, "needed to inhibit the contractive response to inhibit the contractive response after" should read -- needed to inhibit the contractive response after --.

Column 14, lines 8-9, "the way concentration-response dependent the contraction" should read -- the concentration-response dependent contraction --.

Column 14, line 9, "na" should read -- an --.

Column 14, line 13, "derivatives, so that in case" should read -- derivatives, in the case --.

Column 14, line 67, "they came from" should read -- from --.

Column 15, line 11, "NaH2PO4" should read -- NaH$_2$PO$_4$ --.

Column 15, line 11, "NaHCO3" should read -- NaHCO$_3$ --.

Column 15, line 11, "MgC12" should read -- MgCl$_2$ --.

Column 15, line 11, "CaC12" should read -- CaCl$_2$ --.

Column 15, line 22, "(O2, 95% and CO2," should read -- CO$_2$, 95% and CO$_2$," --.

Column 15, line 47, "JM24-1 e JM25-1" should read -- JM24-1 and JM25-1 --.

Column 16, line 16, "they came from" should read -- from --.

Column 17, line 27, "they came from" should read -- from --.

Column 18, lines 20-21, "was so effective" should read -- was as effective --.

Column 18, line 41, "they came from" should read -- from --.

Column 18, line 61-62, "atack introduced by this molecules" should read -- attack introduced by these molecules --.

Column 18, line 67, "condition" should read -- a condition --.

Column 19, line 3, "JM24-1 e JMF2-1" should read -- JM24-1 and JMF2-1 --.